United States Patent [19]
Liu

[11] Patent Number: 5,971,959
[45] Date of Patent: Oct. 26, 1999

[54] AUTOMATIC SAFETY INFUSION CATHETER NEEDLE

[76] Inventor: Wen-Neng Liu, 19508 Nicholas Ave., Cerritos LA., Calif. 90701

[21] Appl. No.: 09/227,877

[22] Filed: Jan. 11, 1999

Related U.S. Application Data

[63] Continuation-in-part of application No. 09/089,260, Jun. 3, 1998, Pat. No. 5,885,252.

[51] Int. Cl.$^6$ .................................................. A61M 5/178
[52] U.S. Cl. ......................................... 604/164; 604/171
[58] Field of Search ........................... 604/164, 165–168, 604/170, 174, 177, 264, 195

[56] References Cited

U.S. PATENT DOCUMENTS

| | | | |
|---|---|---|---|
| 5,830,190 | 11/1998 | Howell | 604/164 X |
| 5,833,662 | 11/1998 | Stevens | 604/167 |
| 5,846,227 | 12/1998 | Osterlind | 604/164 |
| 5,893,844 | 4/1999 | Misawa | 604/164 X |

*Primary Examiner*—John D. Yasko
*Attorney, Agent, or Firm*—Rosenberg, Klein & Bilker

[57] ABSTRACT

An automatic safety infusion catheter needle including: a trifurcate connector having a first and a second connecting sections coaxially aligned with each other; an infusion soft needle inserted on the first connecting section of the trifurcate connector; and a steel needle having a needle body slidably fitted in a sleeve and axially passed in the soft needle. The sleeve is connected with the second connecting section of the trifurcate connector. The holder body of the steel needle has a projecting post formed with an air guiding hole for exhausting the air outside and making the liquid medicine smoothly flow into the soft needle. An infusion catheter is serially connected with a third connecting section of the trifurcate connector for infusion of liquid medicine through the soft needle into the body of a patient. The steel needle is formed with a latching groove and at least one guiding rib is disposed on a lower edge of the latching groove. When pulling back the steel needle out of the sleeve, the guiding rib serves to outward expand the latching flange of bottom end of the sleeve, permitting the latching flange to smoothly latch with the latching groove of the steel needle so as to hide the needle body of the steel needle in the sleeve.

6 Claims, 10 Drawing Sheets

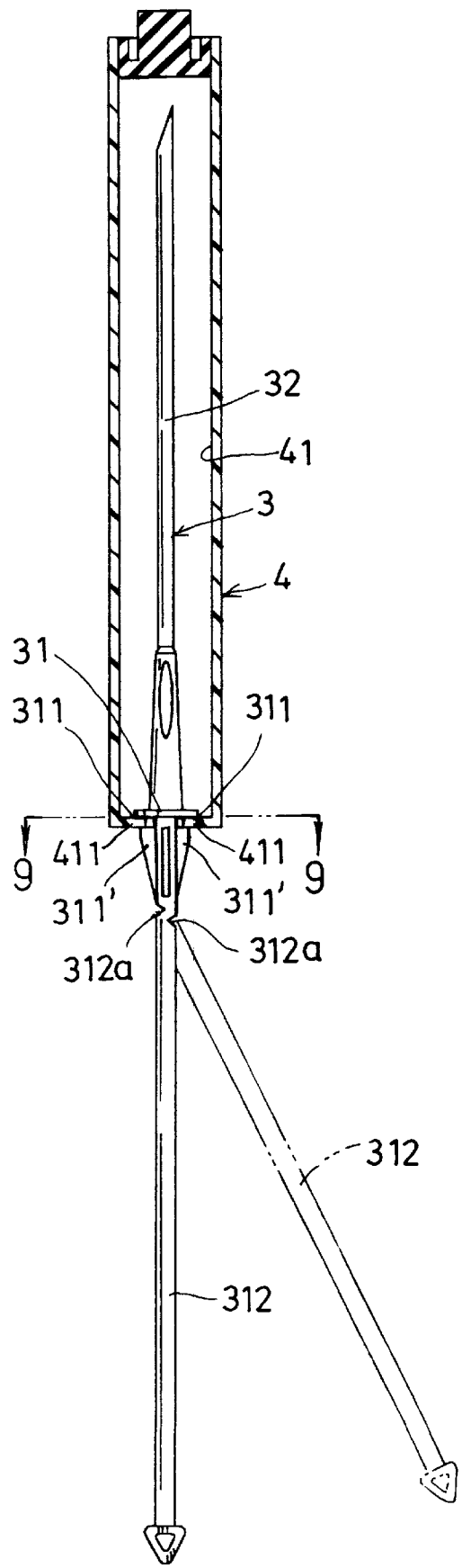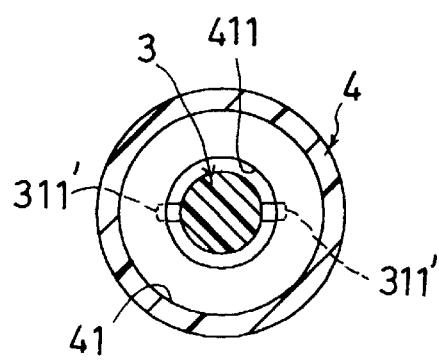
FIG. 9
FIG. 8

AUTOMATIC SAFETY INFUSION CATHETER NEEDLE

CROSS-REFERENCE TO RELATED APPLICATION

This application is a Continuation-in-Part of U.S. patent application Ser. No. 09/089,260, entitled "An Automatic Safety Infusion Catheter Needle", filed on Jun. 3, 1998, now U.S. Pat. No. 5,885.252.

BACKGROUND OF THE INVENTION

Field of the Invention

The present invention relates to an automatic safety infusion catheter needle in which the steel needle is formed with a latching groove and at least one guiding rib is disposed on a lower edge of the latching groove. When pulling back the steel needle out of the sleeve, the guiding rib serves to guide the latching flange of bottom end of the sleeve, permitting the latching flange to smoothly latch with the latching groove of the steel needle so as to firmly locate and hide the needle body of the steel needle in the sleeve.

The existing infusion catheter needle employs one single injection needle for intravenous injection. As shown in FIG. 1, such catheter needle includes an infusion soft needle 100 and a steel needle 200. The needle body 200a of the steel needle 200 is passed through the needle body 100a of the soft needle 100 for hardening the soft needle body 100a, whereby the soft needle body 100a can be smoothly thrusted into the vein of a patient. After the soft needle body 100a is thrusted into the vein, the medical personnel must press the soft needle body 100a with one hand F to avoid back flow of the blood of the patient and draw the steel needle 200 backward from the soft needle 100 with the other hand. Then an infusion catheter 300 is serially connected with the soft needle 100 to complete the injection procedure. In use, the above catheter needle has some shortcomings as follows:

1. When pressing the soft needle body 100a with one hand, the medical personnel must draw the steel needle 200 from the soft needle 100 with the other hand. Moreover, the medical personnel must then connect the infusion catheter 300 with the soft needle 100. It is quite inconvenient to perform all these procedures at the same time.

2. After the steel needle 200 is drawn from the soft needle 100, the steel needle 200 is exposed outside and tends to impale the medical personnel. Therefore, the medical personnel may be infected with AIDS, hepatitis, etc. This is extremely dangerous to the medical personnel.

SUMMARY OF THE INVENTION

It is therefore a primary object of the present invention to provide an automatic safety infusion catheter needle which is able to avoid impalement of medical personnel and ensure the safety in medical waste processing. In addition, the automatic safety infusion catheter needle enables the medical personnel to perform the injection procedure more easily and leisurely.

According to the above object, the automatic safety infusion catheter needle of the present invention includes: a trifurcate connector having a first and a second connecting sections coaxially aligned with each other, a free end of the second connecting section being inserted with a rubber cap; an infusion soft needle fitted with the first connecting section of the trifurcate connector; and a steel needle including a holder body slidably fitted in a sleeve. A top section of the sleeve is fitted with the second connecting section of the trifurcate connector. The steel needle has a projecting post upward axially extending from top end of the holder body. The projecting post is formed with an air guiding hole for exhausting the air outside and making the liquid medicine smoothly flow into the soft needle. The needle body of the steel needle axially upward extends from the projecting post and slidably fitted in the soft needle body of the steel needle axially upward extends from the projecting post and slidably fitted in the soft needle body of the soft needle. An infusion catheter is connected with a third connecting section of the trifurcate connector for infusion of liquid medicine through the soft needle into the body of a patient. Accordingly, in injection, the soft needle together with the needle body of the steel needle is thrusted into the vein of the patient. Then the steel needle is withdrawing from the rear side of the sleeve to retract and locate and hide the needle body of the steel needle in the sleeve so as to avoid impalement and infection of the medical personnel. In addition, the medical personnel can perform the injection procedure leisurely.

The present invention can be best understood through the following description and accompanying drawings, wherein:

BRIEF DESCRIPTION OF THE DRAWINGS

FIG. 8 shows that the steel needle is firmly latched with the sleeve of the present invention;

FIG. 9 is a sectional view taken along line 9—9 of FIG. 8;

DETAILED DESCRIPTION OF THE PREFERRED EMBODIMENTS

Figure 1:
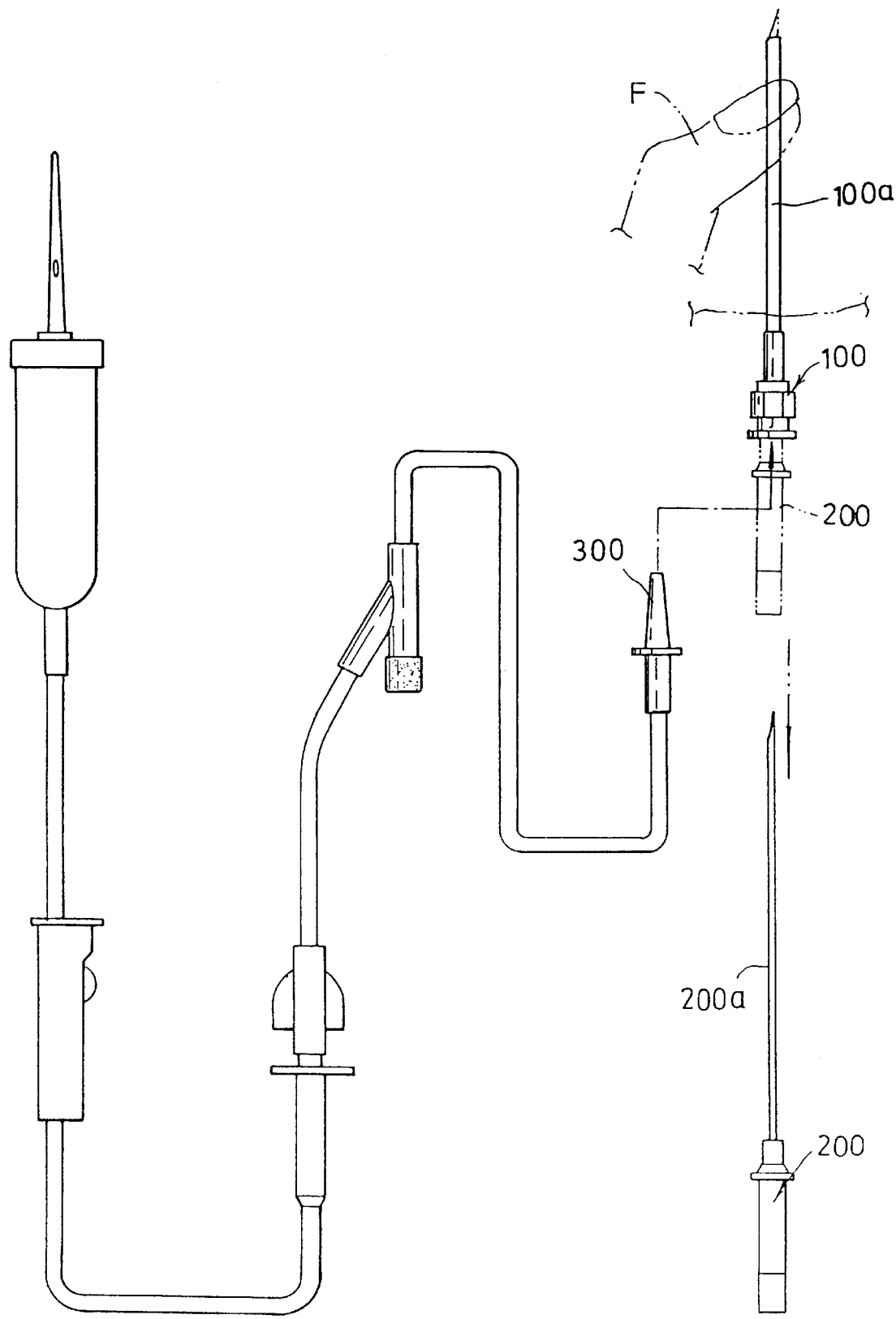
FIG. 1 shows a conventional intravenous catheter needle.
Figure 2:
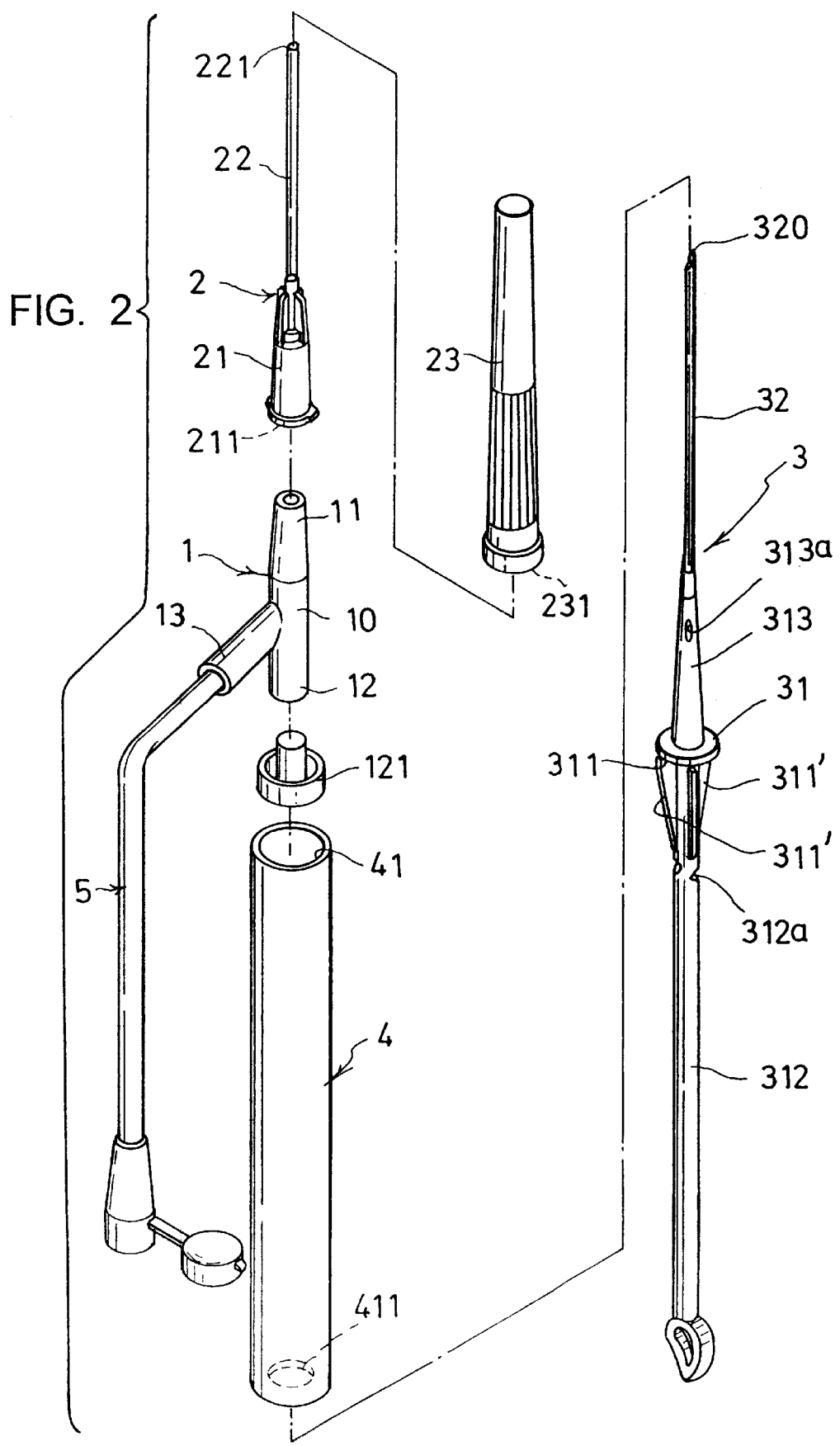
FIG. 2 is a perspective exploded view of the present invention.
Figure 3:
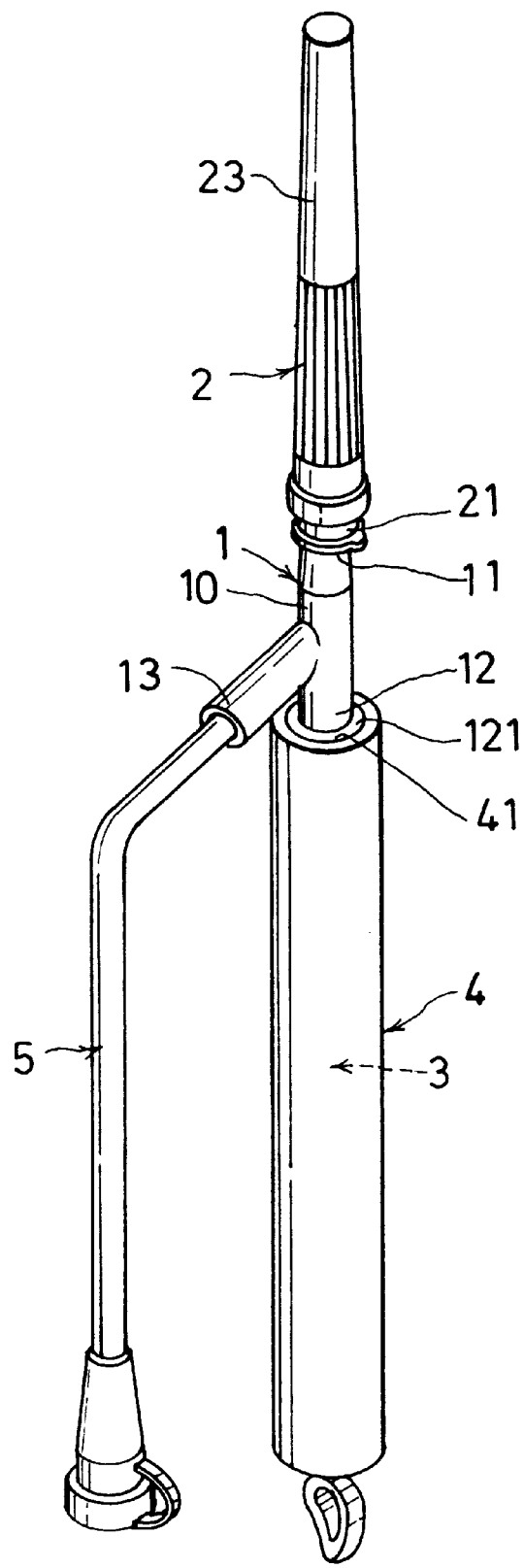
FIG. 3 is a perspective assembled view of the present invention.

Please refer to FIGS. 2 to 10. The present invention includes: a trifurcate connector 1 having a first and a second connecting sections 11, 12 coaxially aligned with each other, the end of the second connecting section 12 being fitted with a rubber cap 121; an infusion soft needle 2 inserted on the first connecting section 11 of the trifurcate connector 1; a steel needle 3 a top end of which is inserted with a needle body 32 axially slidably fitted in the soft needle 2; and a sleeve 4 a top end of which is fitted with the second connecting section 12 of the trifurcate connector 1. The steel needle 3 is slidably received in the sleeve 4. An infusion catheter 5 is serially connected with a third connecting section 13 of the trifurcate connector 1 for infusion of liquid medicine through the soft needle 2 into the body of a patient. Accordingly, in injection, the needle body 32 of the steel needle 3 is first slidably fitted into the soft needle 2 and then the soft needle 2 together with the needle body 32 of the steel needle 3 is thrusted into the vein of the patient. Then the steel needle 3 is withdrawn from the rear side of the sleeve 33 to retract and locate and hide the needle body 32 of the steel needle 3 in the sleeve 4. Therefore, the needle body 32 of the steel needle 3 is prevented from being exposed outside so as to avoid impalement and infection of the medical personnel.

The trifurcate connector 1 is made of plastic material, including a main body 10. An upper section of the main body 10 is defined as the first connecting section 11. A lower section of the main body 10 is defined as the second connecting section 12. The end of the second connecting section 12 is fitted with the rubber cap 121. The first and second connecting sections 11, 12 are coaxially aligned with each other about the central axis 10a of the main body 10. The third connecting section 13 outward projects from a middle section of the main body for connecting with the infusion catheter 5.

The infusion soft needle 2 includes: a needle holder 21 formed with a fitting socket 211 at bottom end for fitting with the first connecting section 11 of the trifurcate connector; a soft needle body 22 upward extending from the top end of the needle holder 21 and formed with an axial injection passage 221; and a needle sheath 23 formed with a protective cavity 231 for fitting around the needle holder 21 to enclose the soft needle body 22.

The steel needle 3 includes: a holder body 31 formed with a latching groove 311, a pulling rod 312 axially extending from the bottom end of the latching groove, a lower edge of the latching groove 311 being formed with at least one guiding rib 311', a projecting post 313 upward extending from the holder body 31, the projecting post 313 being formed with at least one radial through hole 313a; and a needle body 32 inserted with the top end of the projecting post 313 and slidably fitted into the soft needle body 22 of the soft needle 2. A central through hole 320 of the needle body 32 being communicated with the through hole 313a of the projecting post 313. The projecting post 313 is passed through the rubber cap 121 fitted with the second connecting section 12 of the trifurcate connector 1, whereby when the needle body 32 is slidably fitted into the soft needle body 22, the through hole 313a of the projecting post 313 is positioned above the rubber cap 121 to communicate with the infusion catheter 5 connected with the third connecting section 13. Therefore, the liquid medicine can flow out from the through hole 313a through the central hole 320 of the needle body 32.

The guiding rib 311' of the steel needle 3 is downward tapered to form a slope slat for guiding the latching groove 311 of the steel needle 3 to smoothly slidably latch with a latching flange 411 of the sleeve 4.

The sleeve 4 is formed with a central fitting hole 331 axially downward extending from a top end of the sleeve 4. A top end of the sleeve 41 is snugly fitted around the end of the second connecting section 12 of the trifurcate connector 1. A bottom end of the fitting hole 41 is formed with an inward extending latching flange 411 for latching with the latching groove 311 of the steel needle 3.

Figure 10:
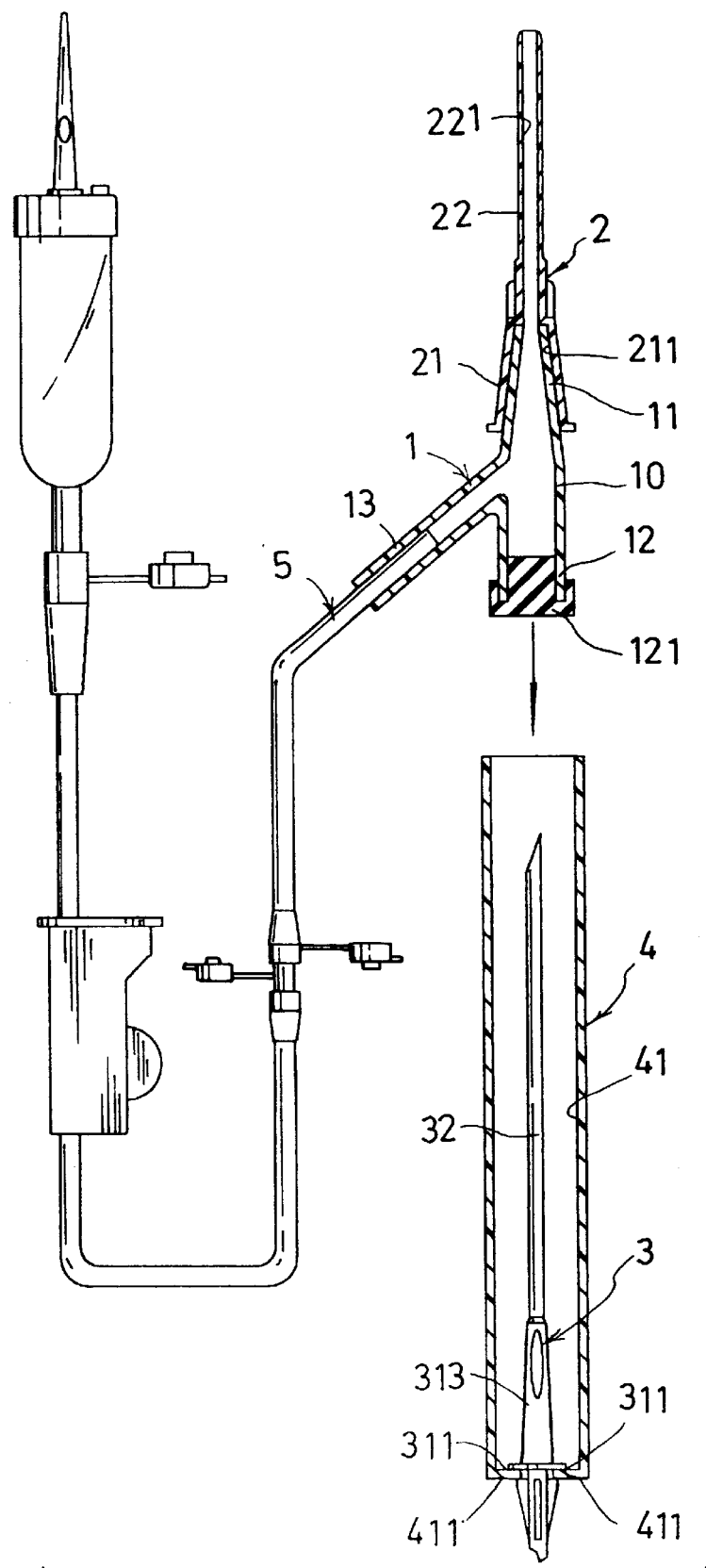
FIG. 10 shows that the steel needle is detached from the trifurcate connector.

The periphery of the top section of the pulling rod 312 of the steel needle 3 is formed with at least one breaking notch 312a, whereby after the pulling rod 311 is pulled back, the pulling rod 312 can be bent and broken at the breaking notch 312a as shown by FIGS. 8 and 10. After removing the sleeve 4, the pulling rod 312 together with the needle body 32 are processed and discarded.

Figure 4:
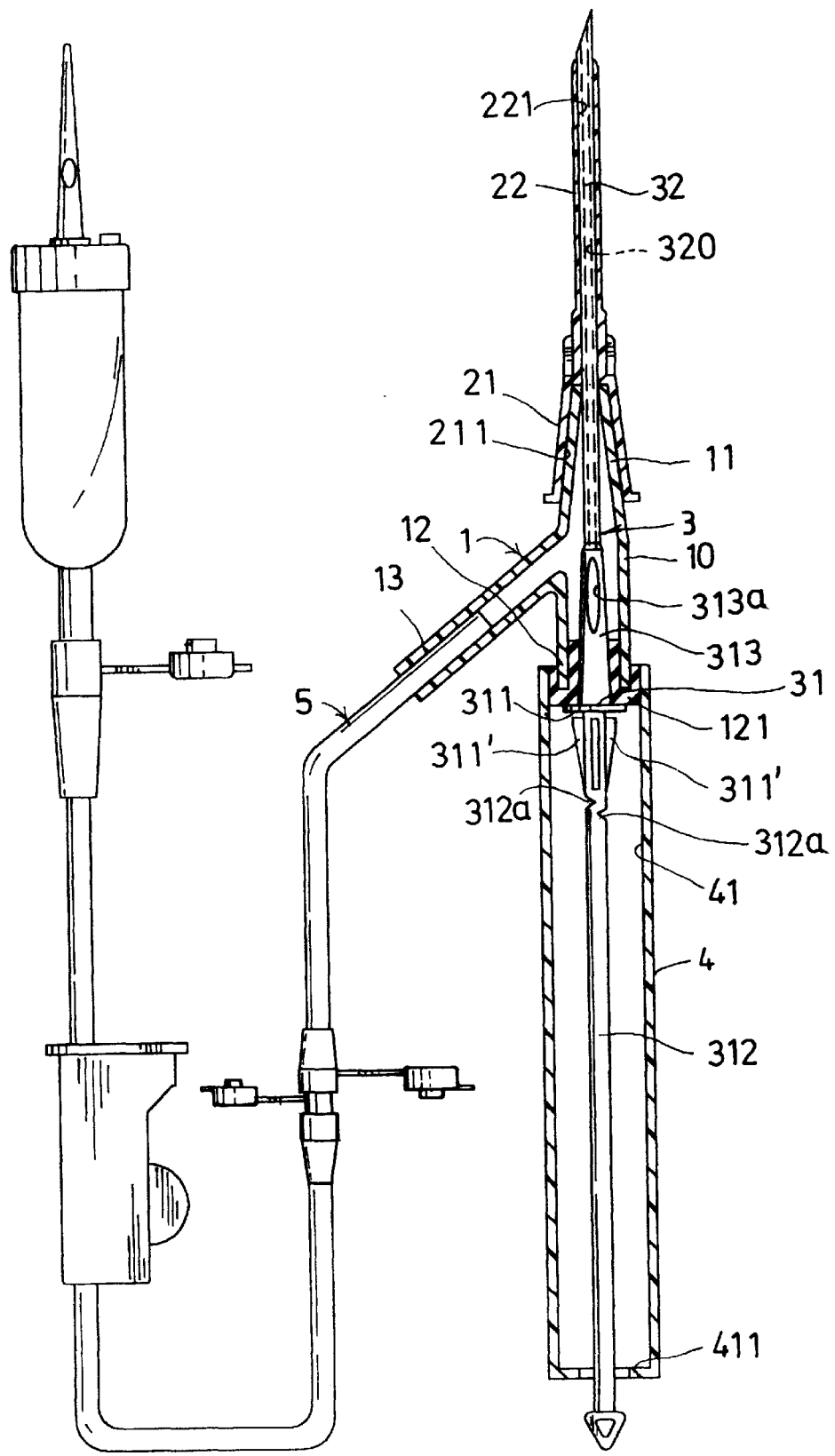
FIG. 4 is a sectional view showing that the steel needle is fitted in the soft needle for thrusting into the body of a patient.
Figure 5:
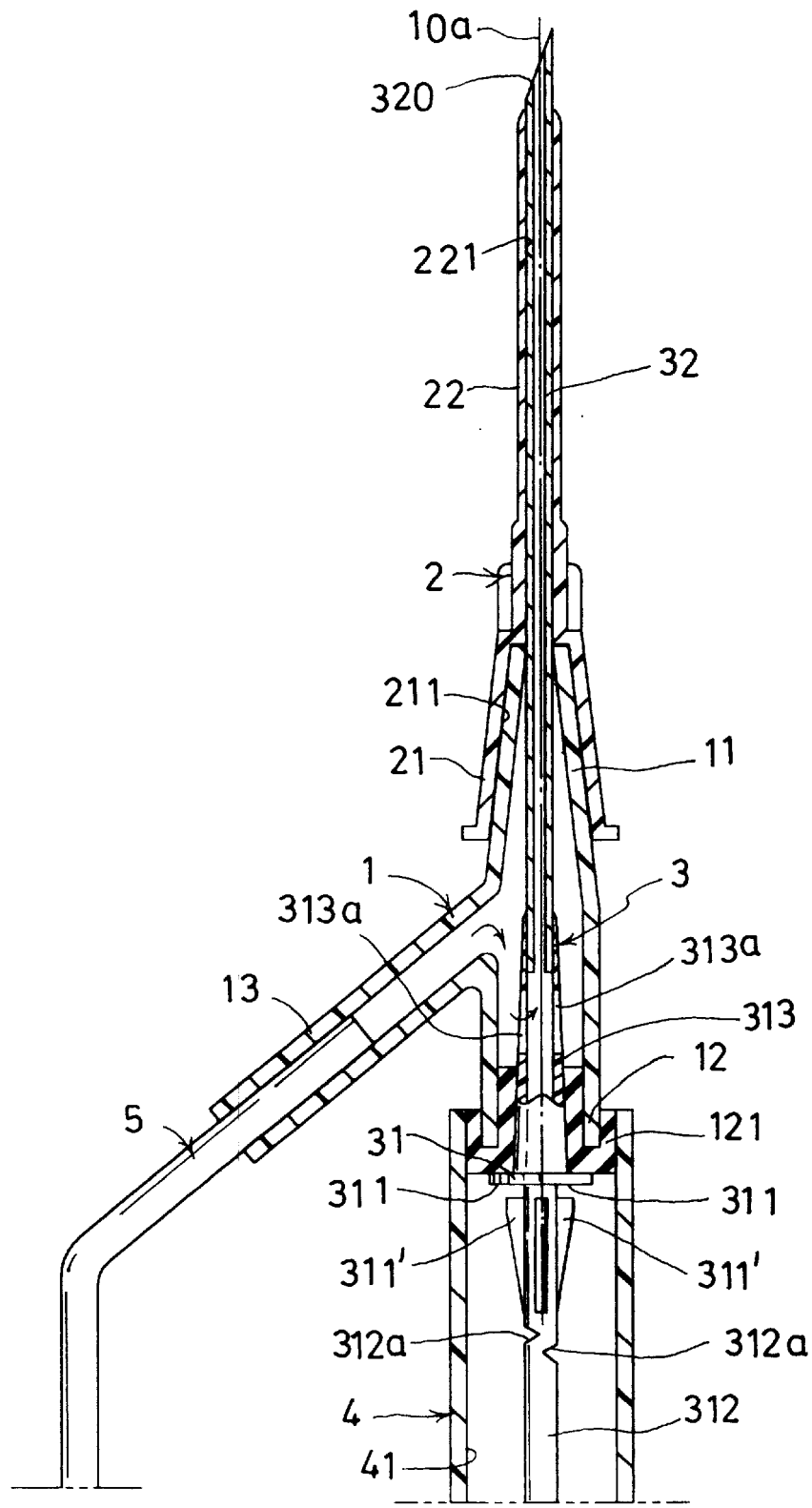
FIG. 5 is an enlarged view of a part of FIG. 4.
Figure 6:
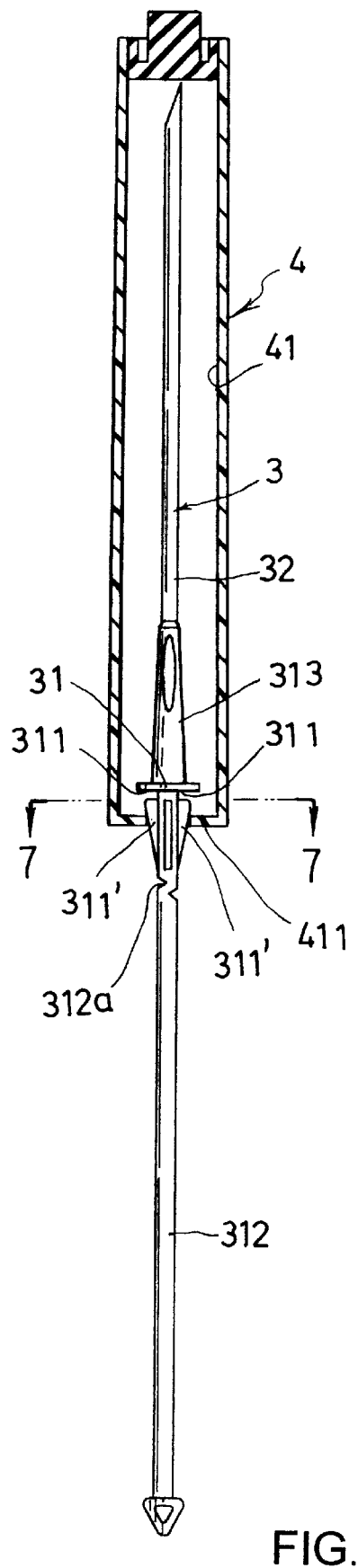
FIG. 6 is a view according to FIG. 3, showing that the steel needle is pulled backward.
Figure 7:
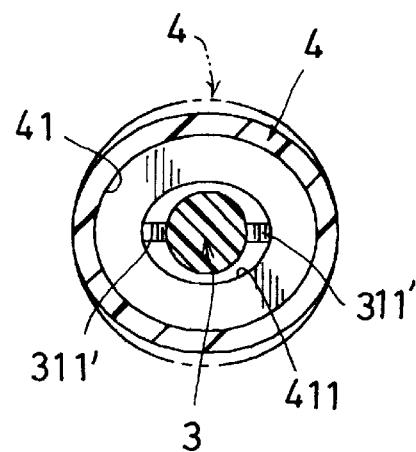
FIG. 7 is a sectional view taken along line 7—7 of FIG. 6.

In use, the infusion catheter 5 is first connected with the third connecting section 13 of the trifurcate connector 1. Then the needle sheath 23 is removed from the soft needle 2. At this time, as shown in FIGS. 4 and 5, the air contained in the infusion catheter 5 is exhausted outside through the through hole 313a of the projecting post of the steel needle 3 and the central through hole 320 of the needle body 32. Therefore, the liquid medicine contained in the infusion catheter 5 (such as a dropper) can smoothly flow out. This makes the infusion catheter 5 and the trifurcate connector 1 full of the liquid medicine so as to prevent the air in the infusion catheter 5 from being injected into human body to cause accident. At this time, the needle body 32 of the steel needle 3 is slidably fitted in the soft needle body 22 of the soft needle 2, providing a sufficient strength therefor to smoothly thrust into the vein of a patient. The rubber cap 121 fitted with the end of the second connecting section 12 resiliently surrounds the bottom end of the projecting post 313 of the steel needle 3, so that the liquid medicine flowing from the infusion catheter 5 into the trifurcate connector 1 will not leak from the second connecting section 12. As shown in FIGS. 4 and 6, thereafter, the medical personnel can pull back the pulling rod 312 and extract the needle body 32 out of the soft needle body 22. When the needle body 32 is totally drawn out of the rubber cap 121, the rubber cap 121 automatically resiliently seals the perforation thrusted by the projecting post 313 and the needle body 32. That is, the opening of the second connecting section 12 of the trifurcate connector 1 is again sealed. Then the pulling rod 312 is further pulled backward to make the guiding ribs 311' of the holder body 31 slide over the latching flange 411 of the sleeve 4. At this time, as shown in FIGS. 6 and 7, the bottom end of the sleeve 4 is slightly expanded into an elliptic shape and the latching flange 411 is slided along the guiding ribs 311' to latch with the latching groove 311 of the steel needle 3. Therefore, the needle body 32 of the steel needle 3 is totally hidden in the fitting hole 41 of the sleeve 4. At this time, as shown in FIGS. 8 and 9, the latching flange 411 is no more forced by the guiding ribs 311' and the sleeve 4 is restored to the circular cross-section and firmly latched in the latching groove 311. Accordingly, the medical personnel can bend and break the pulling rod 312 at the breaking notch 312a as shown by the phantom line of FIG. 8. Then the sleeve 4 is removed and discarded together with the needle body 32 of the steel needle 3. As shown in FIG. 10, when the needle body 32 is totally drawn out of the soft needle body 22, the liquid medicine flowing from the third connecting section 13 into the trifurcate connector 1 will automatically flow from the first connecting section 11 through the soft needle 2 into the body of the patient. In the case that it is necessary to inject other liquid medicine, an injection syringe can be thrusted into the rubber cap 121 at the end of the second connecting section 12 to perform the injection procedure.

Figure 12:
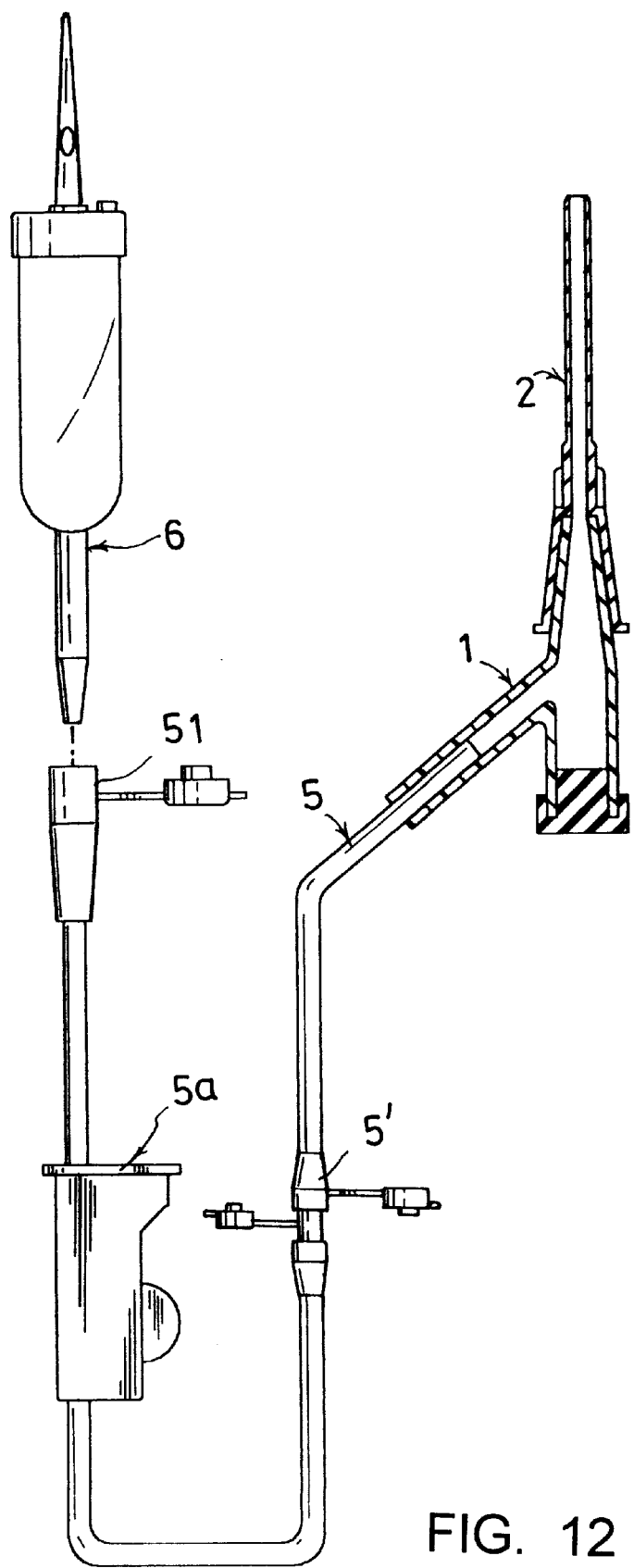
FIG. 12 shows that the dropper infusion throttle tube is separated from the dropper connector of the present invention.

FIG. 12 shows the infusion catheter 5 of the present invention. A tail end connector 5' of the infusion catheter 5 is connected with a dropper infusion throttle tube 5a. An input end of the throttle tube 5a is connected with a connector 51 for connecting with a dropper connector 6 to form a set of dropper syringe. Multiple infusion catheters (not shown) can be serially connected between the dropper connector 6 and the throttle tube 5a so as to prolong the injection distance to meet the requirement. (The existing dropper connector is integrally connected with the throttle tube and cannot be serially connected with other infusion catheter so that the injection distance cannot be prolonged.) Certainly, the infusion catheter 5 of the present invention can be alternatively integrally connected with the throttle tube 5a without the end connector 5'.

Figure 11:
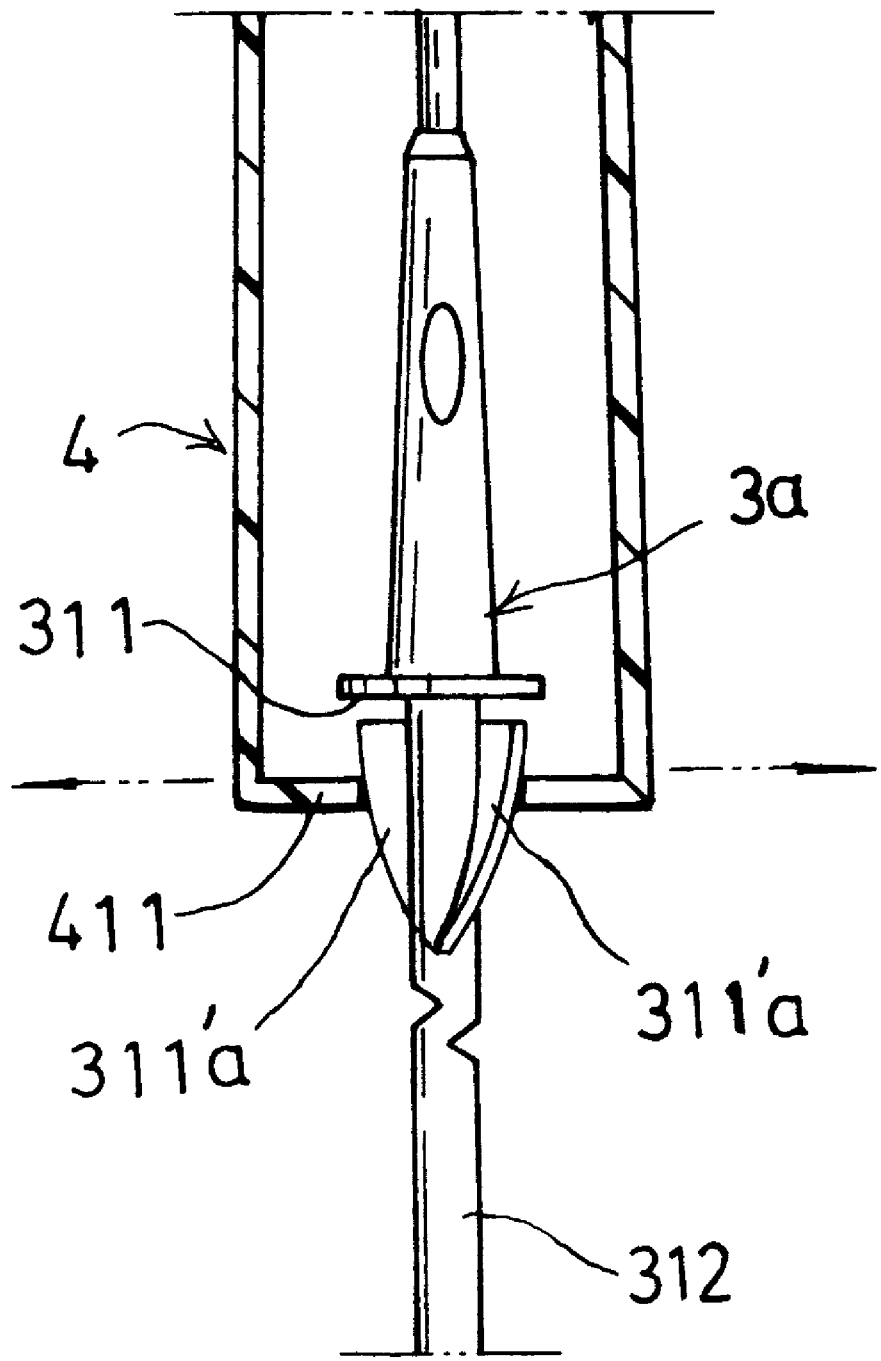
FIG. 11 shows another embodiment of the steel needle of the present invention.

By means of the guiding ribs 311' under the latching groove 311 of the steel needle 3, the steel needle 3 can be smoothly and easily drawn back to latch with the latching flange 411 of the sleeve 4. In addition, FIG. 11 shows a modification of the steel needle 3a in which the guiding ribs 311'a is spiralled around the pulling rod 312 so as to reduce the slope and more smoothly guide A the latching groove 311 of the steel needle 3a to slidably latch with the latching flange 411 of the sleeve 4.

When withdrawing the needle body 32 of the steel needle 3 out of the soft needle body 22, it is unnecessary to press the infusion soft needle 2 with one hand as the conventional device. Therefore, the medical personnel can perform the injection procedure leisurely. The present invention is applicable to medical infusion or liquid medicine or blood with respect to adult, child or animal.

According to the above arrangements, the present invention has the following advantages:

1. The steel needle 3 is formed with at least one guiding rib 311'a under the latching groove 311, whereby the latching groove 311 can be smoothly slidably latched with the latching flange of the sleeve 4.

2. The needle body 32 of the steel needle is latched and hidden in the sleeve 4 without protruding outside. Therefore, the impalement of medical personnel can be avoided.

3. The present invention has simple structure and can be easily operated.

It is to be understood that the above description and drawings are only used for illustrating some embodiments of the present invention, not intended to limit the scope thereof. Any variation and derivation from the above description and drawings should be included in the scope of the present invention.

What is claimed is:

1. An automatic safety infusion catheter needle comprising:

a trifurcate connector having a hollow main body, an upper section of the main body being defined as a first hollow connecting section, a lower section of the main body being defined as a second hollow connecting section, the first and second connecting sections being coaxially aligned with each other about a central axis of the main body, a free end of the second connecting section being inserted with a rubber cap, a third connecting section outward projecting from a section between the first and second connecting sections of the main body for connecting with an infusion catheter;

an infusion soft needle including a needle holder formed with a fitting socket at bottom end for fitting with the first connecting section of the trifurcate connector, a soft needle body connecting with and upward extending from a top end of the needle holder;

a steel needle including a holder body formed with a latching groove, a pulling rod axially extending from a bottom end of the latching groove, a lower edge of the latching groove being formed with at least one guiding rib, a projecting post upward extending from the holder body, the projecting post being formed with at least one radial through hole, a needle body being connected with a top end of the projecting post and passed through the second connecting section and slidably fitted into the soft needle body of the soft needle; and a sleeve formed with a central fitting hole, a top end of the sleeve being snugly fitted around the second connecting section of the trifurcate connector, a bottom end of the fitting hole being formed with an inward extending latching flange, the steel needle being slidably fitted in the fitting hole with the latching groove latched with the latching flange of the sleeve so as to firmly locate the needle body of the steel needle in the sleeve.

2. An automatic safety infusion catheter needle as claimed in claim 1, wherein the guiding rib of the steel needle is downward tapered.

3. An automatic safety infusion catheter needle as claimed in claim 1, wherein the guiding rib of the steel needle is downward tapered and spiralled.

4. An automatic safety infusion catheter needle as claimed in claim 1, wherein the pulling rod is formed with at least one breaking notch at the top end thereof.

5. An automatic safety infusion catheter needle as claimed in claim 1, wherein the infusion catheter is serially connected with a dropper infusion throttle tube, an input end of the throttle tube is connected with a connector for serially connecting with a dropper connector.

6. An automatic safety infusion catheter needle as claimed in claim 5, wherein the infusion catheter is integrally connected with the throttle tube.

* * * * *